(12) United States Patent
Wang et al.

(10) Patent No.: US 7,504,834 B2
(45) Date of Patent: Mar. 17, 2009

(54) DETECTION SYSTEM

(75) Inventors: Ding Wang, Austin, TX (US); Steven Y. Yu, Austin, TX (US)

(73) Assignee: 3M Innovative Properties Company, St. Paul, MN (US)

( * ) Notice: Subject to any disclaimer, the term of this patent is extended or adjusted under 35 U.S.C. 154(b) by 110 days.

(21) Appl. No.: 11/613,670

(22) Filed: Dec. 20, 2006

(65) Prior Publication Data

US 2008/0150555 A1   Jun. 26, 2008

(51) Int. Cl.
G01R 27/08 (2006.01)

(52) U.S. Cl. ............... 324/693; 324/649; 73/587; 73/803; 73/862.046; 205/791

(58) Field of Classification Search ............ 324/693, 324/700, 71.2; 73/86; 202/404
See application file for complete search history.

(56) References Cited

U.S. PATENT DOCUMENTS

| | | | |
|---|---|---|---|
| 3,907,656 A * | 9/1975 | de Souza | ............ 522/81 |
| 4,380,763 A | 4/1983 | Peart et al. | |
| 4,780,664 A | 10/1988 | Ansuini et al. | |
| 4,962,360 A | 10/1990 | Homma et al. | |
| 5,195,046 A | 3/1993 | Gerardi et al. | |
| 5,260,520 A | 11/1993 | Muhs et al. | |
| 5,310,470 A | 5/1994 | Agarwala et al. | |
| 5,323,429 A | 6/1994 | Roarty et al. | |
| 5,338,432 A | 8/1994 | Agarwala et al. | |
| 5,367,583 A | 11/1994 | Sirkis | |
| 5,746,905 A * | 5/1998 | Murray | ............ 205/791 |
| 5,859,537 A | 1/1999 | Davis et al. | |
| 6,012,337 A * | 1/2000 | Hodge | ............ 73/803 |
| 6,054,038 A | 4/2000 | Davis et al. | |
| 6,063,486 A | 5/2000 | Kobayashi | |
| 6,144,026 A | 11/2000 | Udd et al. | |
| 6,316,646 B1 | 11/2001 | Tacke et al. | |
| 6,320,137 B1 | 11/2001 | Bonser et al. | |
| 6,328,878 B1 | 12/2001 | Davis et al. | |
| 6,342,295 B1 | 1/2002 | Kobayashi | |
| 6,355,301 B1 | 3/2002 | Miller | |
| 6,384,610 B1 | 5/2002 | Wilson | |
| 6,399,939 B1 | 6/2002 | Sundareson et al. | |
| 6,445,565 B1 | 9/2002 | Toyoda et al. | |
| 6,896,779 B2 | 5/2005 | Thomas, III et al. | |

(Continued)

FOREIGN PATENT DOCUMENTS

EP   1 434 048 A1   6/2004

(Continued)

Primary Examiner—Timothy J Dole
Assistant Examiner—Benjamin M Baldridge
(74) Attorney, Agent, or Firm—Gregg H. Rosenblatt

(57) ABSTRACT

A detection system for monitoring an engineered structure includes an array of sensors disposable in a predetermined pattern on the engineered structure and disposable between a surface of the engineered structure and a protective coating substantially covering the surface. The detection system also includes a controller in communication with the array of sensors for retrieving data from the sensors. The controller communicates with the sensor array via an optical fiber backbone. The array of sensors can remotely provide data corresponding to at least one of a degree of cure of the protective coating, a health of the cured protective coating, and a corrosion rate of the engineered structure at each of the sensors.

16 Claims, 8 Drawing Sheets

U.S. PATENT DOCUMENTS

| | | |
|---|---|---|
| 6,911,828 B1 * | 6/2005 | Brossia et al. ............... 324/649 |
| 7,117,742 B2 * | 10/2006 | Kim ............................ 73/587 |
| 7,244,500 B2 | 7/2007 | Watts et al. |
| 2002/0078752 A1 | 6/2002 | Braunling et al. |
| 2002/0153873 A1 | 10/2002 | Shapiro et al. |
| 2004/0045365 A1 | 3/2004 | Richardson |
| 2004/0047050 A1 * | 3/2004 | Bauer et al. ................. 359/738 |
| 2004/0189331 A1 | 9/2004 | Girshovich et al. |
| 2005/0006251 A1 | 1/2005 | Thomas, III et al. |
| 2005/0034985 A1 | 2/2005 | Zamanzadeh et al. |
| 2005/0036135 A1 | 2/2005 | Earthman et al. |
| 2005/0046860 A1 | 3/2005 | Waagaard et al. |
| 2005/0082467 A1 | 4/2005 | Mossman |
| 2006/0247896 A1 * | 11/2006 | Goldfine et al. ............. 702/183 |
| 2007/0120572 A1 | 5/2007 | Chen et al. |
| 2007/0144272 A1 * | 6/2007 | Yu et al. ................. 73/862.046 |

FOREIGN PATENT DOCUMENTS

| | | |
|---|---|---|
| JP | 09-318462 | 12/1997 |
| JP | 2001-133214 | 5/2001 |
| WO | WO 2004/031738 A1 | 4/2004 |
| WO | WO 2004/031739 A2 | 4/2004 |
| WO | WO 2004/065942 A1 | 8/2004 |

* cited by examiner

DETECTION SYSTEM

BACKGROUND

1. Field of the Invention

The present invention is directed to a detection system.

2. Related Art

Sensors capable of detecting corrosion are known, such as is described in U.S. Pat. Nos. 6,384,610; 6,328,878; 6,316,646; 5,859,537; 6,054,038; 6,144,026; 4,380,763; 4,780,664; 4,962,360; 5,323,429; 5,367,583; 6,445,565; and 6,896,779. For example, while some of these conventional approaches utilize "embeddable" corrosion sensors, the conventional technologies often employ rigid printed circuit boards and rigid silicon wafer chips. Limitations of such technology include thickness and fragility—placing rigid circuit boards under thin epoxy or paint coatings can cause disruptions in the coating, and silicon wafer-based sensors are prone to fractures, and do not conform to uneven surfaces.

SUMMARY OF THE INVENTION

According to a first aspect of the present invention, a detection system for monitoring an engineered structure includes an array of sensors disposable in a predetermined pattern on the engineered structure and disposable between a surface of the engineered structure and a protective coating substantially covering the surface. The detection system also includes a controller in communication with the array of sensors for retrieving data from the sensors. The controller communicates with the sensor array via an optical fiber backbone. The array of sensors can provide data corresponding to at least one of a degree of cure of the protective coating, a health of the cured protective coating, and a corrosion rate of the engineered structure at each of the sensors.

The above summary of the present invention is not intended to describe each illustrated embodiment or every implementation of the present invention. The figures and the detailed description that follows more particularly exemplify these embodiments.

BRIEF DESCRIPTION OF THE DRAWINGS

The present invention will be further described with reference to the accompanying drawings, wherein.

Figure 1A:
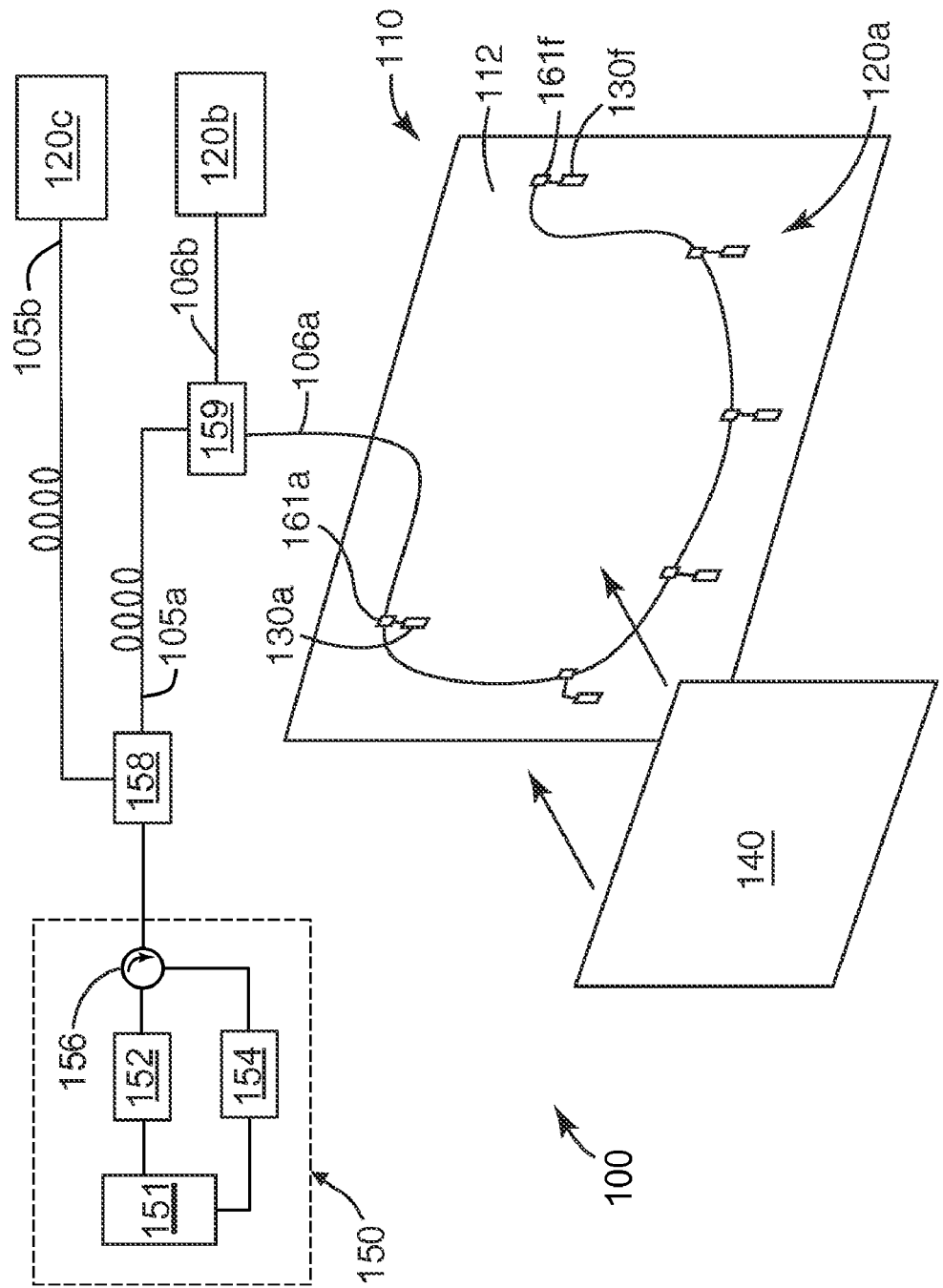
FIG. 1A is an exemplary detection system according to an embodiment of the present invention.

While the invention is amenable to various modifications and alternative forms, specifics thereof have been shown by way of example in the drawings and will be described in detail. It should be understood, however, that the intention is not to limit the invention to the particular embodiments described. On the contrary, the intention is to cover all modifications, equivalents, and alternatives falling within the scope of the invention as defined by the appended claims.

DETAILED DESCRIPTION OF THE EMBODIMENTS

The present invention is directed to a detection system. In particular, the detection system of the exemplary embodiments is embeddable and can be utilized to detect several key characteristics of a coated surface on an engineered structure. In addition, the detection system utilizes an optical fiber backbone or network to link one or more arrays of detectors with a central control system. The optical fiber backbone provides for long distance connections and a substantial reduction or elimination of electromagnetic interference (EMI) signal degradation. The detection system can be utilized to detect the degree of cure of a coating that is applied to the surface of an engineered structure. In addition, the detection system can be utilized to detect the health of the coating after cure, e.g., by detecting the deterioration of the coating (e.g., moisture ingress) when exposed to natural elements. Further, the detection system can be utilized to detect the integrity of the surface of the engineered structure, e.g., by detecting physical conditions that promotes corrosion.

In these exemplary implementations, the detection system can be configured to provide real-time, periodic (e.g. per hour, per day, per week) data related to one or more physical conditions of an engineered structure through a data acquisition system. This type of data acquisition system can provide for "condition-based" maintenance for engineered structures, as opposed to "preventive" maintenance, which is currently used. Thus, the detection system of the exemplary embodiments can help maximize the operational life of an engineered structure or object by providing real-time data to better manage the scheduling of repairs or replacements of such objects or structures. In addition, the use of an optical backbone allows for a controller system to be located at a far distance (e.g., 10 km or more, as measured by the length of the optical fiber transmission line) from the engineered structure being monitored.

According to an exemplary embodiment of the present invention, FIG. 1A shows a detection system 100 in schematic view. The detection system 100 includes a central controller 150 linked to a sensor array 120a via a transmission optical fiber 105a. In this exemplary embodiment, sensor array 120a includes a plurality of sensors (in this example, a group of six (6) sensors (130a-130f) are shown for simplicity) coupled to a data transmission fiber 105a/106a. The sensor array 120a is disposed on a surface 112 of an engineered structure 110. As is explained in further detail below, the embodiments of the present invention can utilize different types of sensors. For example, in some embodiments, a corrosion sensor configuration having a cathode-anode structure can measure impedance, current, and/or voltage to monitor corrosion. Other types of sensors, such as chemical detectors, can also be utilized.

In an exemplary embodiment, a coating 140 is applied to the surface 112 of the engineered structure 110. The sensors 130a-130f are configured to have a very thin design (e.g., having a sensing portion thickness of about 13 μm to about 75 μm) so that the sensors are easily disposed between the surface 112 and the coating 140. In this manner, the sensors can simultaneously provide data on the health of the coating 140 and the engineered structure 110.

The engineered structure 110 can be any type of structure or object that is exposed to natural elements, such as water, rain, wind, etc. The physical composition of the structure 110 can be a metal, such as steel, a carbon fiber composite, a ceramic, or a fiberglass based material such as a fiberglass laminate.

In an exemplary embodiment, the detection system 100 can be utilized in a marine platform (e.g., boat, submarine) to detect the health of the coatings and/or structures within a ballast tank or other water-holding structures. As is understood, ballast tanks are used in marine platforms to provide ballast for the vessel. These tanks can be continually filled and/or drained and can also collect debris and other materials. As salt water is a very corrosive substance, real-time, periodic coating and/or structure health assessments detected by exemplary detection system 100 can provide critical information related to maintenance planning.

According to alternative embodiments, detection system 100 can be used with other types of engineered structures, such as tunnels, bridges, pipes, and aircraft, which are also susceptible to corrosion or other forms of physical deterioration. For example, sensors can be distributed along the length of an underwater/underground oil pipeline that is difficult to visually inspect due to physical boundaries. The remote sensing attributes of embodiments of the present invention can provide a user the ability to query sensors from many kilometers away.

To protect structures 110, coating 140 can comprise a coating, such as an epoxy-based coating or paint, such as polyamide epoxies (e.g., an epoxy meeting MIL- spec. 24441) and coating epoxies (e.g., product no. 2216 A/B, available from 3M Company, St. Paul, Minn.). As is explained further below, detection system 100 can be used to detect characteristics such as the cure condition and/or health of coating 140.

In accordance with an exemplary embodiment, central controller 150 can be remotely located from the particular engineered structure 110 being monitored. In a preferred aspect, controller 150 includes a data acquisition system 151 coupled to a light source 152 and a spectrum analyzer 154.

An optical signal generated by the light source 152 is communicated to the sensor array 120a via a transmission optical fiber 105a. In a preferred aspect, the controller 150 sends and receives optical signals. The return optical signals can be distributed to the optical spectrum analyzer 154 via an optical circulator 156. Optionally, an optical switch 158, controlled by the controller 150, can be utilized to distribute the optical signal to other engineered structures and/or other sensor arrays, such as sensor array 120c. The use of an optical signal to communicate with the one or more sensor arrays of the overall system provides for long distance connections and a substantial reduction or elimination of electromagnetic interference (EMI) signal degradation.

In one aspect, data acquisition system 151 can be configured as a server or other computer-based device that communicates with light source 152, optical spectrum analyzer 154, and (optionally) optical switch 158. Data acquisition system 151 can include an interface device and a computer for data storage and display. Also, the data acquisition system can be coupled to a separate display to provide graphical data, such as real-time coating condition data, to a user. As the data acquisition system 151 can be a computer, server, or computer-based device, data collection, manipulation, analysis, and delivery can be provided via application-specific software programs loaded thereon. Similar data retrieval, decoding and storing processes can be utilized for all sensors or sensor groups used in the system. If a sensor indicates that a degradation of coating or structure has occurred, an alert can be provided to the user (e.g., in audible and/or visual format). Otherwise, data can be displayed upon user request. An automated process can be employed to activate data retrieval and analysis in a real-time, periodic manner.

In one aspect, light source 152 comprises a continuous broadband source (e.g., a lamp), with a (relatively) low spectrum power density. For example, a source such as an amplified spontaneous emission source can be used to provide an optical signal having a total optical power of about 200 mw over a bandwidth of about 30 nm (with a center wavelength at 1550 nm). Alternatively, light source 152 can include a set of narrower band sources, each having an output at a different wavelength, yielding an output signal of light having multiple separate wavelength channels $\lambda_1$-$\lambda_n$. For example, the set of narrower band sources can comprise a set of diode sources, such as laser diodes, each having a different output wavelength $\lambda_1$-$\lambda_n$. For example, diodes having different wavelength outputs of $\lambda_1$-$\lambda_n$ (e.g., 1550 nm, 1550.5 nm, 1551 nm, 1570 nm) can be used separately. As a further alternative, light source 152 can include a tunable laser that produces laser output at a wider wavelength range (e.g., with laser output spanning a 10-20 μm range). In another alternative, light source 152 can be a modulated light source to help increase sensitivity of the signal acquisition. In yet another alternative, light source 152 can include a combination of broadband and fixed wavelength or tunable wavelength laser sources.

The multi-wavelength optical signal is transmitted to a first sensor array 120a along optical fiber 105a. Optical fiber 105a can be a conventional telecommunications fiber, such as a SMF28™ Optical Fiber available from Corning, Inc. (Corning, N.Y.) or a different optical fiber that is operational at a wavelength region outside the typical optical telecommunication wavelength regions 1300 nm or 1550 nm. Optionally, the optical signal can be further distributed to an additional sensor array 120b via switch 159.

As shown in the embodiment of FIG. 1A, the optical signal (having wavelengths $\lambda_1$-$\lambda_n$) that is received at sensor array 120a can be distributed to the individual sensors 130a-130f via a series of tap-off devices 161a-161f. In a preferred aspect, tap-off device 161a can comprise a power tap, distributing a portion of the incoming signal (e.g., about 1% of the signal) to sensor 130a, while the remaining signal is distributed to the other sensors of the array, sensors 130b-130f. In a preferred aspect, devices 161a-161f can each comprise a 1 by 2 fiber-based power splitter or a 1 by 2 optical coupler.

Figure 1B:
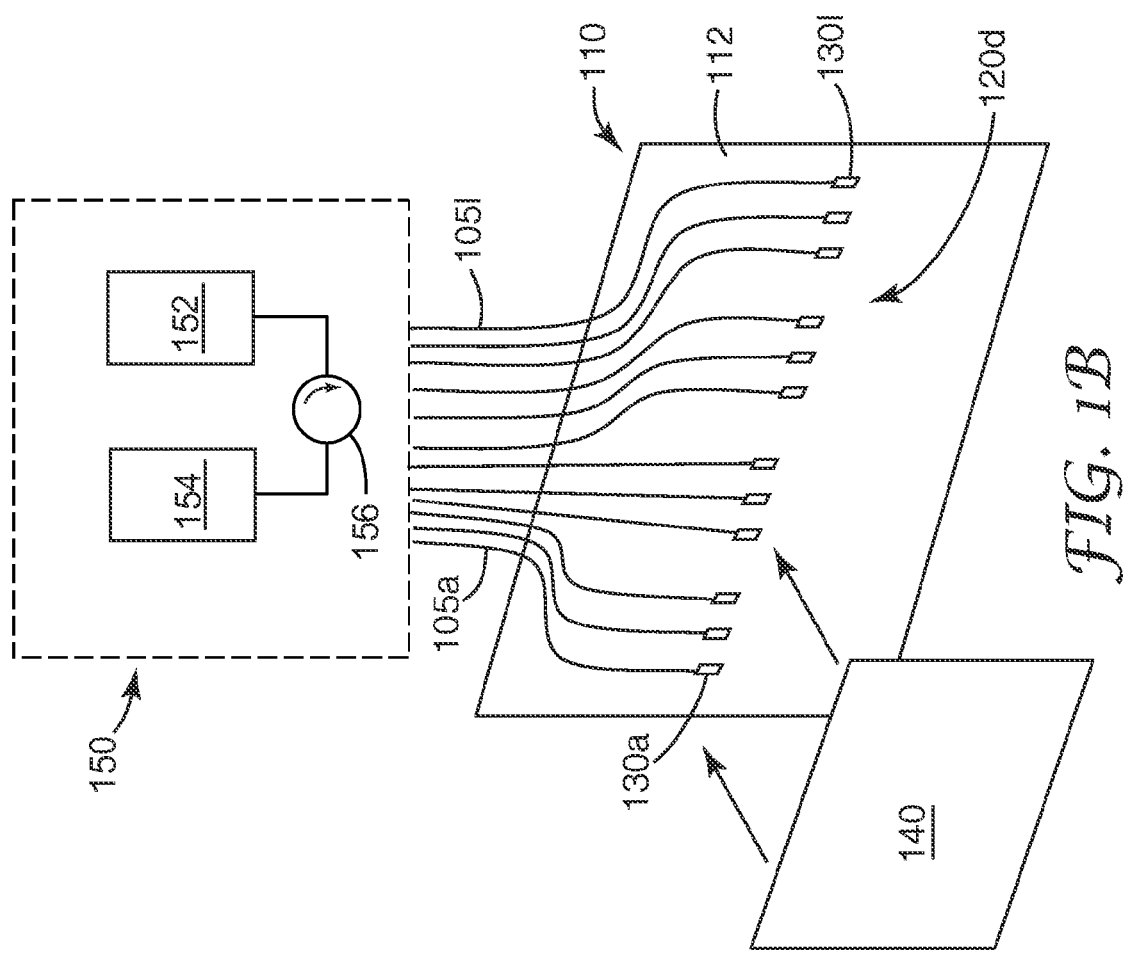
FIG. 1B is an exemplary detection system according to an alternative embodiment of the present invention.

In an alternative embodiment, as shown in FIG. 1B, sensor array 120d can comprise a plurality of individual sensors (in this example, sensors 130a-130l). Here, each individual sensor is coupled directly to the controller 150 (e.g., through optical fibers 105a-105l).

Figure 2:
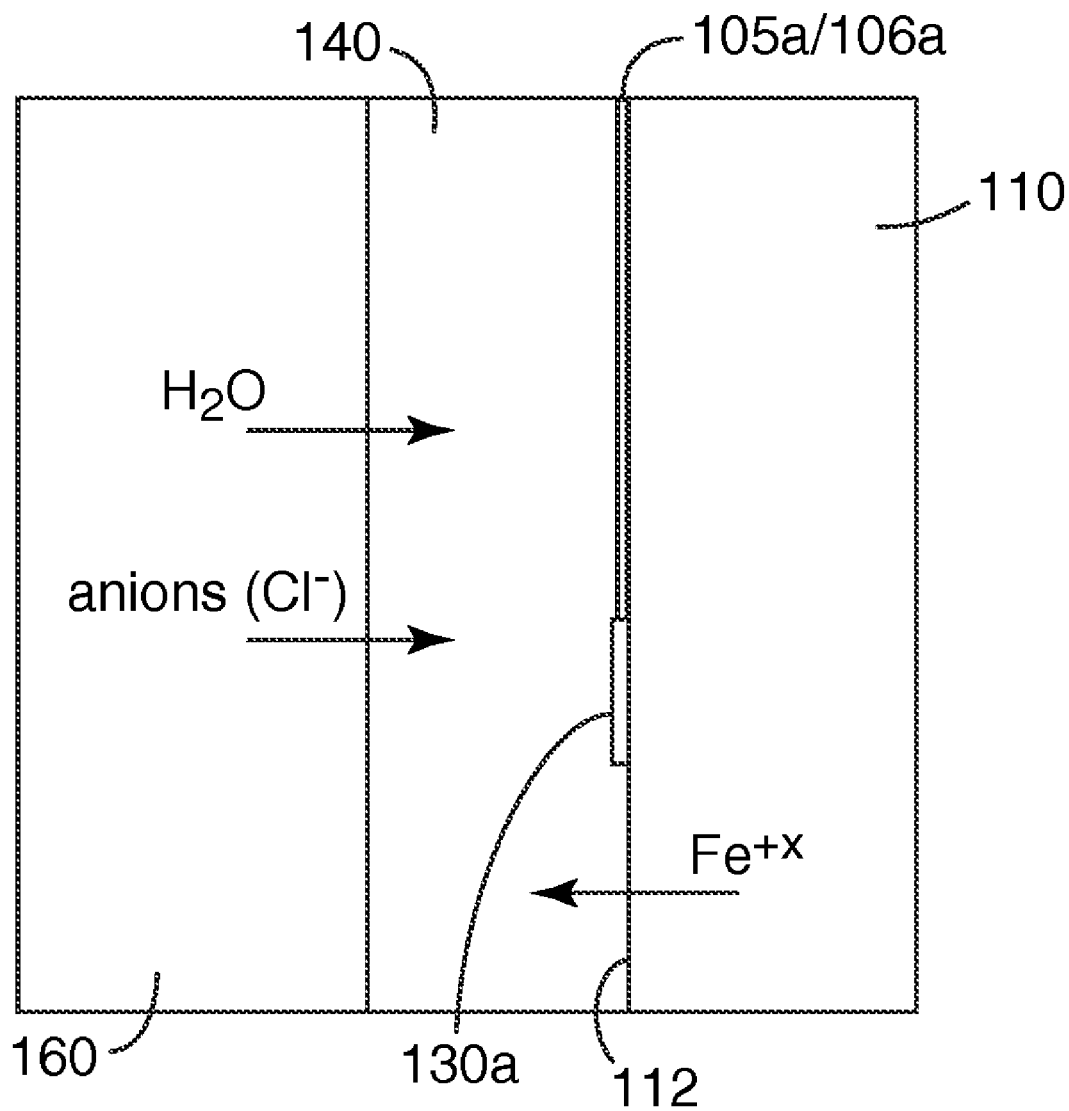
FIG. 2 is a cross-section view of a sensor embedded between a coating and an engineered structure according to an exemplary embodiment of the present invention.

As shown in the cross-section view of FIG. 2, a sensor 130a can be disposed on surface 112 of structure 110, such as a ballast tank. Sensor 130a can be secured to surface 112 via an adhesive, such as a moisture resistant 2-part epoxy (e.g., a Tra-Con 2151 adhesive, available from Tra-Con Corp., Bedford, Mass.), or a double-sided tape or transfer adhesive, such as 3M VHB, available from 3M Company, St. Paul, Minn. Sensor 130a can communicate to the controller 150 via optical fiber 105a/106a. Coating 140 is applied to the surface 112 to protect the structure 110 from the corrosive effects of an external substance or material, such as seawater 160. As is explained in more detail below, sensor 130a can detect the health of the coating 140 (e.g. monitoring the impedance by detecting the presence of chemical species, such as chloride), which indicates general coating health as coating 140 deteriorates and as structure 110 starts to corrode.

Figure 3A:
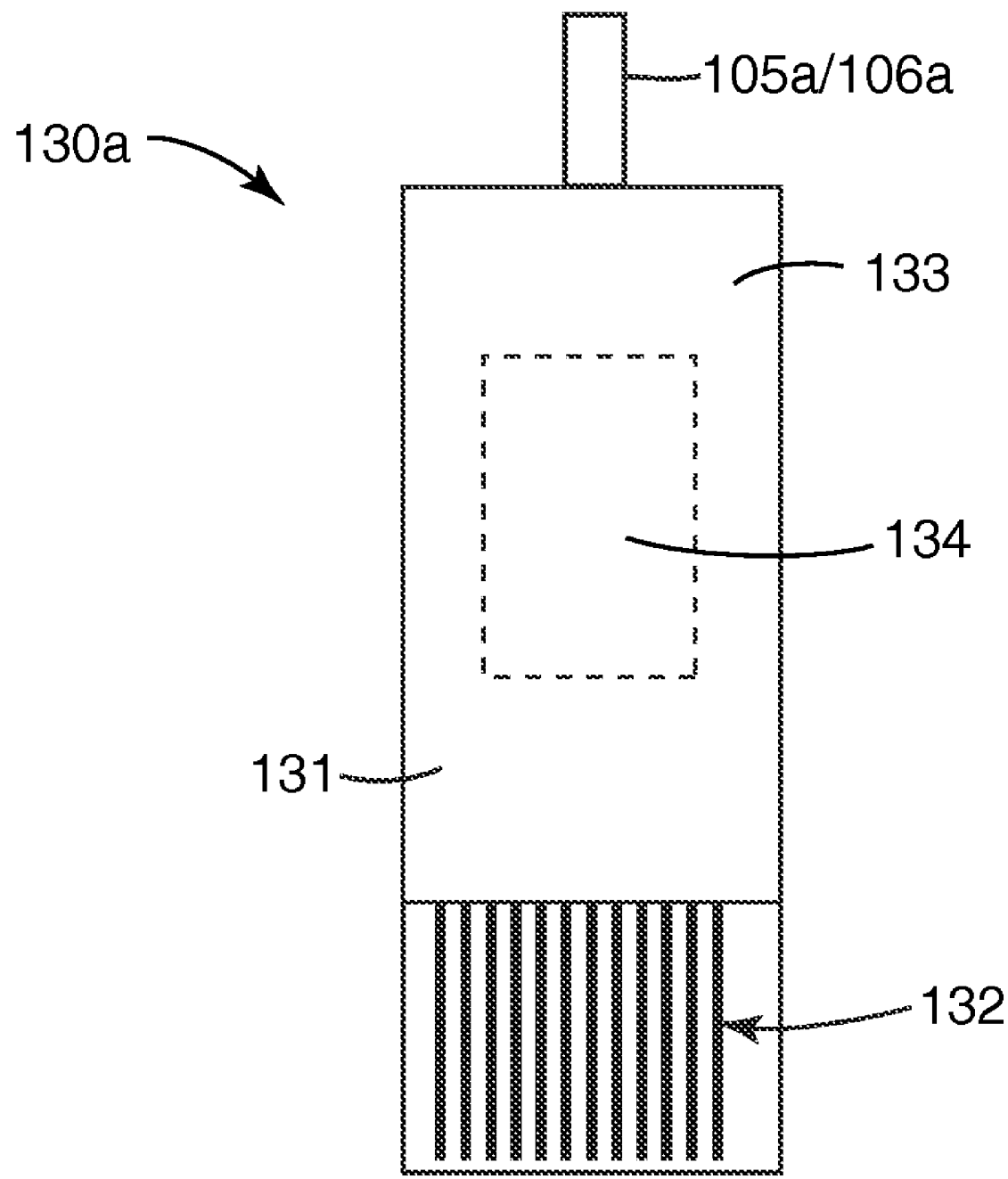
FIG. 3A is an exemplary sensor according to an embodiment of the present invention.
Figures 3B, 3C:
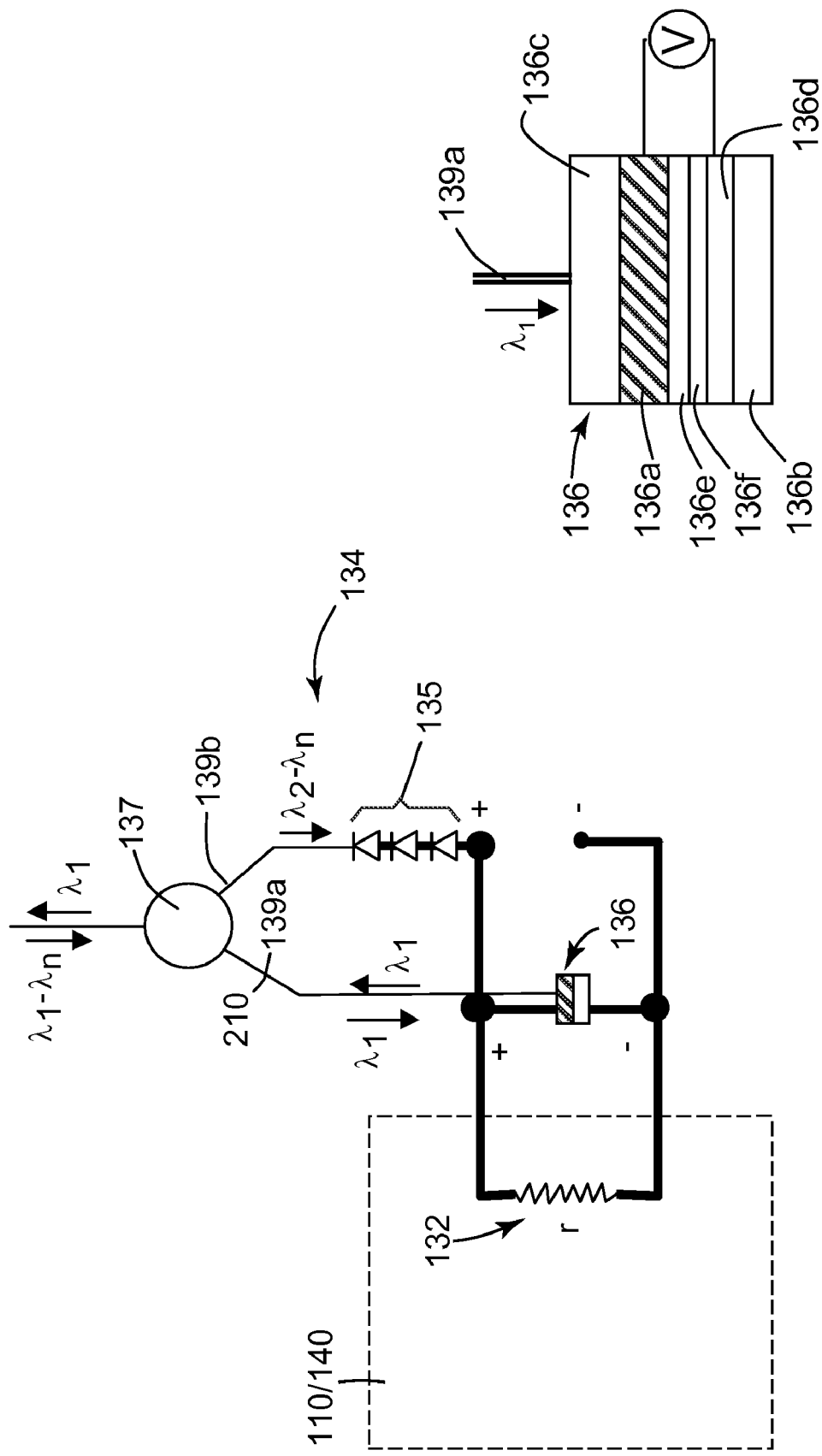
FIG. 3B is a schematic diagram of a portion of an exemplary sensor according to another alternative embodiment of the present invention.
FIG. 3C is a schematic view of the electro-chromic switch of FIG. 3B.

As shown in FIG. 1A, sensor array 120a can include several individual sensors 130a-130f. Of course, a greater number of sensors or a fewer number of sensors can be utilized in sensor array 120a, depending on the size of the engineered structure or the particular application. In a preferred aspect, each individual sensor can have the same basic structure. For example, as shown in FIGS. 3A and 3B, sensor 130a can be formed on a flexible polyimide substrate (described in more detail below) and can include an optoelectronic interface 134 disposed thereon. Alternatively, individual sensors can have different structures.

In one aspect, the optoelectronic interface 134 can be disposed on a base material, such as a polymer-based material, e.g., a polyamide, polyester, liquid crystal polymer or an acrylic material. The base material can provide support for the optoelectronic interface 134 and/or part of a hermetic seal with a cap portion (not shown). The base material and/or other portions of the sensor may be adhered to the surface of the engineered structure 110 by an adhesive, such as VHB adhesive available from 3M Company (St. Paul, Minn.). A protective coating or encapsulant 133 can also be provided to protect the components and interconnects from exposure. Optionally, for further protection, a package cap material, such as a hard plastic, can provide an outer protective shell. The overall package thickness can be kept to about 100 μm to about 1000 μm.

The optoelectronic interface 134 can include an optical signal demultiplexer 137 (see FIG. 3B). In one aspect, the demulitplexer 137 can comprise a thin film-based channel selector that selects a single predefined channel (e.g., $\lambda_1$). Moreover, the optical signal demultiplexer of each sensor can be used to identify each individual sensor by its wavelength $\lambda_n$. The optical signal demultiplexer 137 can be used to split the optical signals in two paths, e.g. paths 139a and 139b, as is shown in FIG. 3B. In one aspect, demulitplexer 137 selects a signal $\lambda_1$ and sends it along path 139a, while the remaining signal $\lambda_2$-$\lambda_n$ is sent along path 139b.

Sensor 130a can further include a PIN diode array 135 to receive and convert a portion of the optical signal into electrical power. As shown schematically in FIG. 3B, the signal $\lambda_2$-$\lambda_n$ is sent along path 139b to the PIN diode array 135, which receives the optical signal and generates electrical power. The electrical power can be used as a power source for an electro-chromic switch 136, which receives another portion of the optical signal split by optical signal demultiplexer 137. In this exemplary aspect, the signal $\lambda_1$ is sent along path 139a to the electro-chromic switch 136. As is described below, the amount of power available to the electro-chromic switch 136 can depend on the condition of the protective coating 140, as the sensing portion 132 is coupled to the power source for the electro-chromic switch 136.

As shown in FIG. 3C, the electro-chromic switch 136 includes two optically transmissive materials 136c, 136d having a voltage-sensitive material 136a disposed therebetween. Voltage-sensitive material 136a can comprise, e.g., tungsten trioxide. An electrolyte, 136e is disposed between the voltage sensitive material and layer 136f, preferably a vanadium pentoxide layer. Electrolyte layer 136e provides a charge transfer mechanism for the applied voltage V, where the vanadium pentoxide layer 136f can enhance the contrast ratio during the turning on and off of the electro-chromic switch. Further, at least one of the transmissive materials, such as transmissive material 136d can be coated with a highly reflective coating 136b. The operation of the electro-chromic switch 136 is described in further detail below.

Figure 6A:
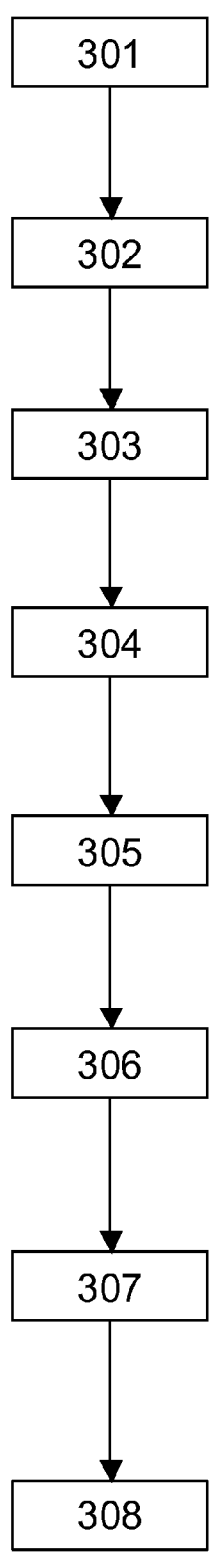
FIGS. 6A and 6B show a method of making an alternative electrochromic switch assembly for use in the sensor system of the current invention.
Figure 6B:
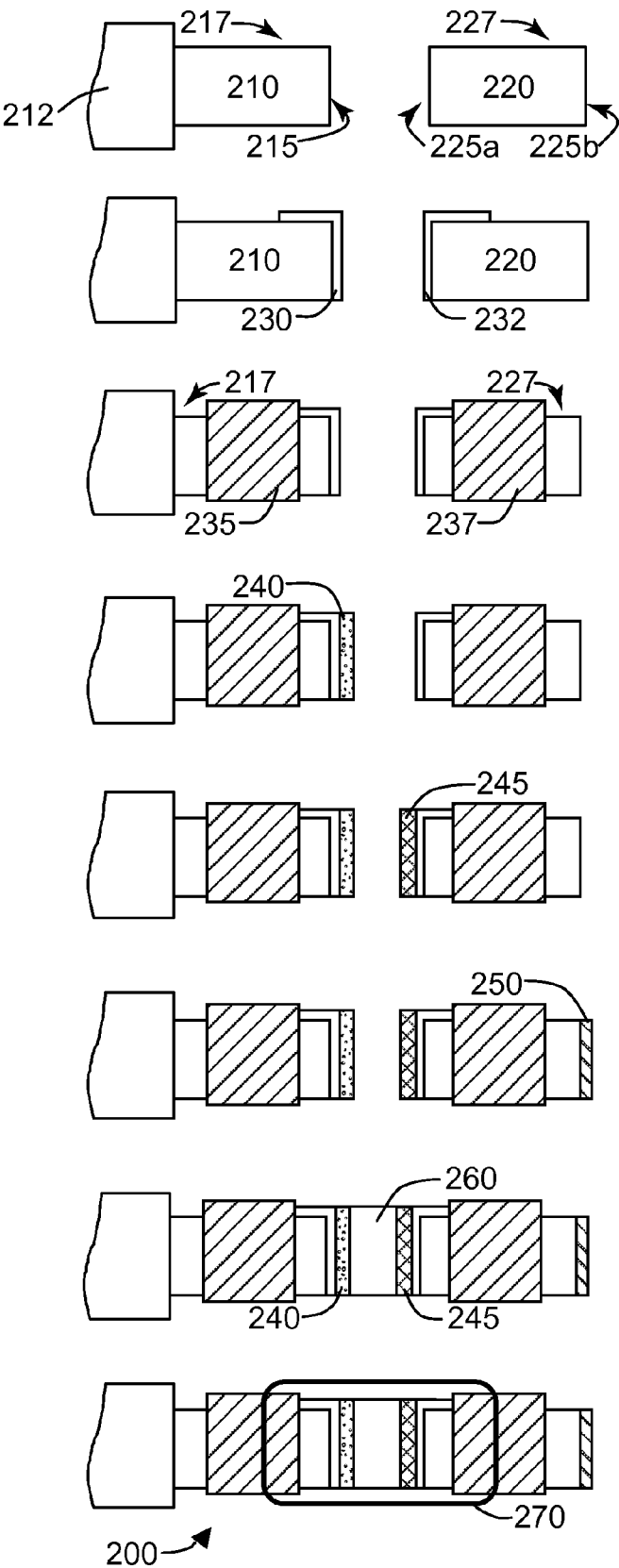

In another aspect, a micro-electro-chromic switch can be utilized in the optoelectronic interface 134 as an alternative to the structure 136 shown in FIG. 3C. In particular, FIGS. 6A and 6B illustrate a process for manufacturing a fiber based electro-chromic switch 200, and the components thereof. As shown, switch 200 can be an extremely compact structure, formed on the terminal end of an optical fiber 210, such as the optical fiber comprising path 139a shown in FIG. 3B.

Referring to FIGS. 6A and 6B, in step 301, the section of an optical fiber that will be used to fabricate the micro-electro-chromic switch 200 is prepared. An optical fiber 210 can be prepared by cleaving the fiber to produce a terminal end 215. The terminal end of the optical fiber 210 can be stripped of its protective polymer coatings 212 using concentrated acid solution, such as a 95% sulfuric acid solution. The rate of optical fiber stripping can vary with temperature and is preferably about 60 seconds at 150° C. A second optical fiber 220 is also utilized, with its terminal end 225a also prepared in a similar manner.

In step 302, a layer of indium tin oxide (ITO) 230, 232 can be deposited onto the sides and terminal ends 215, 225a of optical fiber 210 and fiber 220, respectively. In an exemplary embodiment, the ITO layer is deposited using a standard vacuum sputtering technique. The thickness of the ITO layer may be from about 100 nm to about 200 nm.

In step 303, electrical contacts 235, 237 are formed. The voltage source supplied by the PIN diode array 135 can be connected to the electro-chromic switch 200 via contacts 235, 237. The contacts may be formed using a vacuum deposition process, electroplating process, an electroless platting process or a combination thereof to deposit at least one conductive layer. In an exemplary embodiment, the conductive layer comprises a metal layer selected from gold, copper, nickel and/or silver. The conductive layer can be deposited using an electroless metallization process, such as the process described in U.S. Pat. No. 6,355,301, incorporated herein by reference in its entirety.

In one exemplary embodiment, a nickel layer band is electrolessly plated onto the fiber surfaces 217, 227 such that it overlaps the ITO glass layer. The nickel layer may have a thickness of about 0.1 μm to about 0.2 μm. On top of this nickel layer, an additional thickness of nickel can be electrolytically plated to provide a nickel band with a thickness of about 1 μm. Further, a layer of gold can be electroplated on top of the nickel band to a thickness of about 0.1 μm to complete the contact structure.

In step 304, a tungsten oxide ($WO_3$) material 240 can be applied onto the ITO layer 230 on the terminal end of optical fiber 210 by a conventional process, such as a vacuum sputter deposition process or dip coating process. When using a dip coating, an aqueous solution of $WO_3$ can be used. The tip of the fiber 210 can be placed into the solution, withdrawn and dried (e.g., at 170° C. for 20 minutes) to yield a tungsten oxide layer having a thickness of at least about 100 nm. The thickness of the tungsten oxide layer can be varied according to the electro-chromic switch contrast ratio desired by, for example, changing the concentration of the tungsten oxide solution or by applying multiple applications of the aqueous solution.

In step 305, a vanadium oxide ($V_2O_5$) material 245 can be applied onto the ITO layer 232 on the terminal end of optical fiber 220 by a conventional process, such as a vacuum sputter deposition process or dip coating process. When using a dip coating, an aqueous solution of $V_2O_5$ can be used. The tip of the fiber 220 can be placed into the solution, withdrawn and dried (e.g., at 170° C. for 20 minutes) to yield a vanadium oxide layer having a thickness of at least about 100 nm. The thickness of the vanadium oxide layer can be varied according to the electro-chromic switch contrast ratio desired by, for example, changing the concentration of the vanadium oxide solution or by applying multiple applications of the aqueous solution.

In step 306, fiber 220 can be cut, such that only a small portion of fiber 220 is utilized. In addition, a reflective coating or mirror 250 can be coated on the second terminal end 225b of optical fiber segment 220. In one aspect, the mirror 250 can be formed by metallization. The mirror 350 may be formed using a conventional process, such as a vacuum deposition process, an electroplating process, an electroless plating process, a dip coating or a combination thereof to deposit at least one reflective layer. The reflective layer may comprise silver, aluminum or a series of coating layers having alternating refractive indices. In an exemplary embodiment, the mirror can have a thickness of at least about 150 nm.

In step 307, a polymer electrolyte 260 can be placed between the $WO_3$ layer 240 on optical fiber 210 and the $V_2O_5$ layer 245 on fiber segment 220. The polymer electrolyte preferably comprises a UV-curable polymer electrolyte containing lithium such as a lithium trifluoromethanesulfonimide electrolyte. The electrolyte can be applied by dipping the $WO_3$ coated on optical fiber 210 into an uncured solution of the polymer electrolyte. The $V_2O_5$ coated fiber segment 220 can then be brought into contact with the electrolyte.

In step 308, the assembly can be inserted into a UV-transmissive ferrule such as a glass ferrule to protect the electrochromic switch. The ferrule may be bonded to optical fiber 210 and fiber segment 220 by an adhesive at either end of the ferrule.

The packaged assembly can be exposed to UV light to cure the polymer electrolyte in step 308. The thickness of the cured polymer electrolyte layer can be from about 1 µm to about 100 µm.

Electrical wires can be soldered to the metallized electrical contacts to connect the electrochromic switch to the pin diode array. In an exemplary embodiment, a standard lead-tin or silver soldering process may be used.

As shown in FIG. 1A, sensor 130a further includes a sensor portion 132. In a preferred aspect, array sensing portion 132 can include an electrode structure having interdigitated metal-based (e.g., gold, silver, copper) circuits, which can be used as anodes and cathodes for electrochemical/corrosion measurements, and can be formed on a flexible polyimide substrate. In addition, a portion of sensor 130a can be coated with its own protective overcoat 133 (e.g., covering the electrical/optical conversion portion of the sensor, but leaving sensing portion 132 exposed to the structure 110 and coating 140).

In an exemplary embodiment, sensing portion 132 is formed on a thin, flexible substrate material, such as 3M's flexible circuit material, available under the trade name 3M™ Flex, from 3M Company, St. Paul, Minn. An exemplary article and process for making such a flexible circuit are described in U.S. Pat. No. 6,320,137, incorporated by reference in its entirety. By "flexible", it is meant that the sensor and (if applicable) substrate can be bent so that the sensing portion does not delaminate (e.g., the sensing portion can undergo 90 degree (or greater) bend at a very small radius of curvature, or even a sharp right angle or being creased, without losing its conductive qualities).

For example, the sensing portion 132 can include a substrate, such as a polyimide material. The sensor electrode structure can be formed as a patterned multilayer material upon substrate having, for example, a chrome tie layer, a copper (or other conductive) layer disposed thereon, and a silver (or gold or other metal) layer disposed on the copper layer. Other multi-layer structures can be utilized, as would be apparent given the present description. Thus, a sensing portion 132 with an exemplary cathode-anode structure can provide the ability to measure a voltage drop between the cathode and anode, a current level between the cathode and anode, and/or measure impedance between the cathode and anode, at previously difficult-to-monitor locations.

In an alternative embodiment, the sensing portion 132 can be configured as an electrode formed of a chemical species that is sensitive to water, such as Al, Fe, or Zn. When the chemical species interacts with water, there will be a change in the measured impedance or resistance. Other corrosion sensitive species can also be utilized, as would be apparent to one of ordinary skill in the art given the present description.

In operation, in one aspect, the electro-chromic switch 136 is powered by the output of PIN diodes 135. As shown in the schematic diagram of FIG. 3B, the sensing portion 132, which preferably has a physical construction of an electrode structure having interdigitated metal-based circuits formed on a flexible polyimide substrate, is represented as a resistor electrically coupled to the electro-chromic switch 136.

For example, at the initial stages, the quality of coating 140 is good. Accordingly, the resistance/impedance due to sensing portion 132 is high. As a result, the voltage (V) across the electro-chromic switch 136 is high (e.g., 3V). When the voltage (V) across the electro-chromic switch 136 is high, the voltage-sensitive material 136a absorbs incoming signal ($\lambda_1$) so that no $\lambda_1$ signal is reflected back to the controller 150, as shown in FIG. 1A. At later stages, after exposure to corrosive elements, the quality of coating 140 deteriorates. Accordingly, the resistance/impedance due to sensing portion 132 is decreased. As a result, the voltage (V) across the electro-chromic switch 136 is reduced. When the voltage (V) across the electro-chromic switch 136 is lower, the voltage-sensitive material 136a begins to transmit more of the incoming signal ($\lambda_1$) so that some $\lambda_1$ signal is reflected off coating 136d and sent back to the controller 150. As the coating condition worsens, more $\lambda_1$ signal is reflected back to the controller 150. Thus, the operator can determine the relative health of the coating 140 at a remote location. Other variations of this operation can also be utilized, as would be apparent to one of ordinary skill in the art given the present description.

Figure 4:
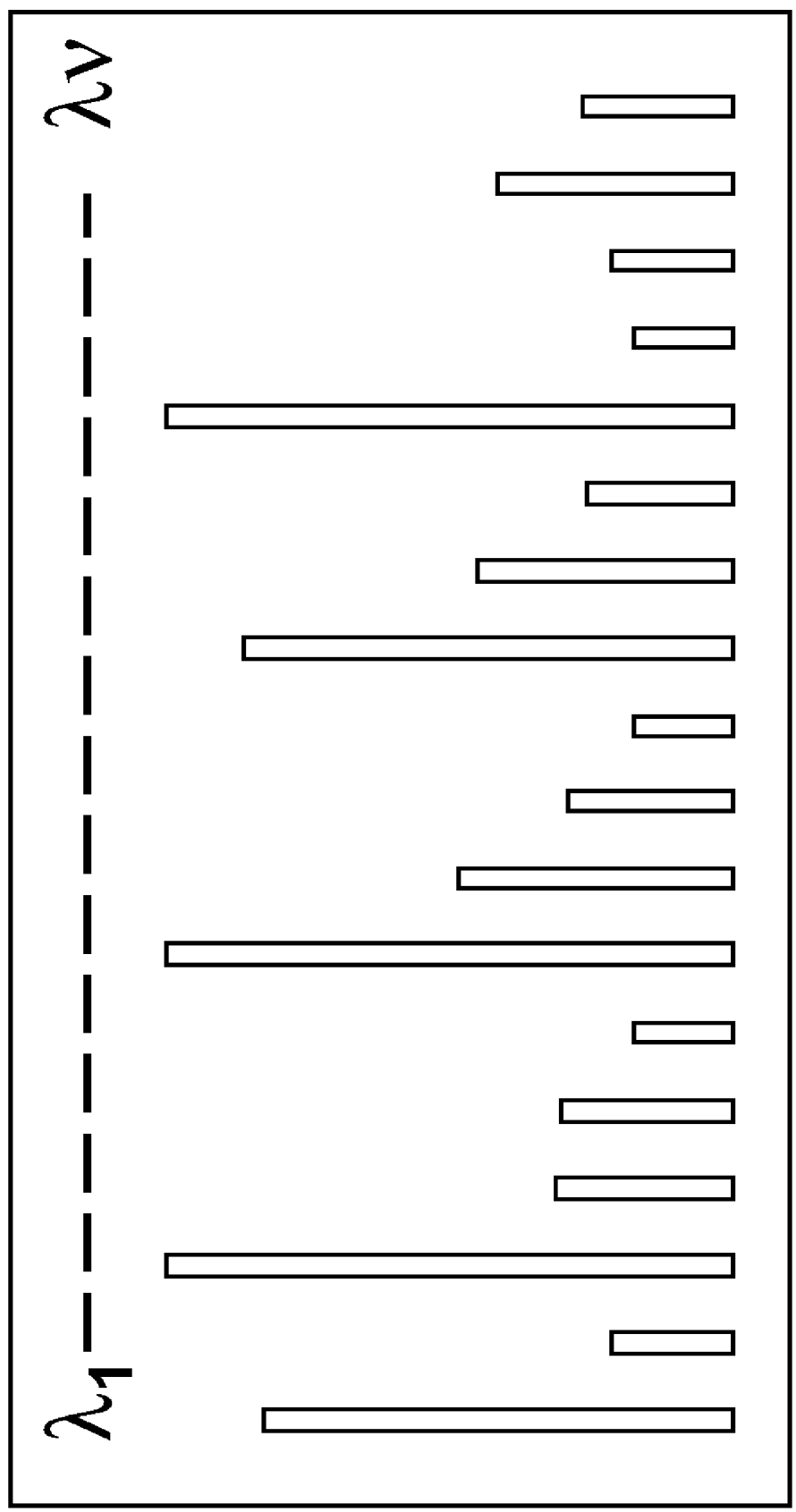
FIG. 4 is an exemplary display output from an example spectrum analyzer.

In a preferred aspect, other signals ($\lambda_2$-$\lambda_n$) at other sensors locations (130b-130n) are generated corresponding to the coating health at the other locations of the engineered structure. Thus, a spectrometer device, such as an optical spectrum analyzer 154 can be used to analyze the reflected light signal. FIG. 4 shows an exemplary display output from an example spectrum analyzer 154, where signal strength at particular wavelengths (e.g., $\lambda_1$-$\lambda_n$) can provide the operator with corresponding coating conditions at different locations of the engineered structure. Moreover, the use of an optical fiber backbone provides for long distance connections (e.g., 10 km or more) and a substantial reduction or elimination of electromagnetic interference (EMI) signal degradation.

Figure 5A:
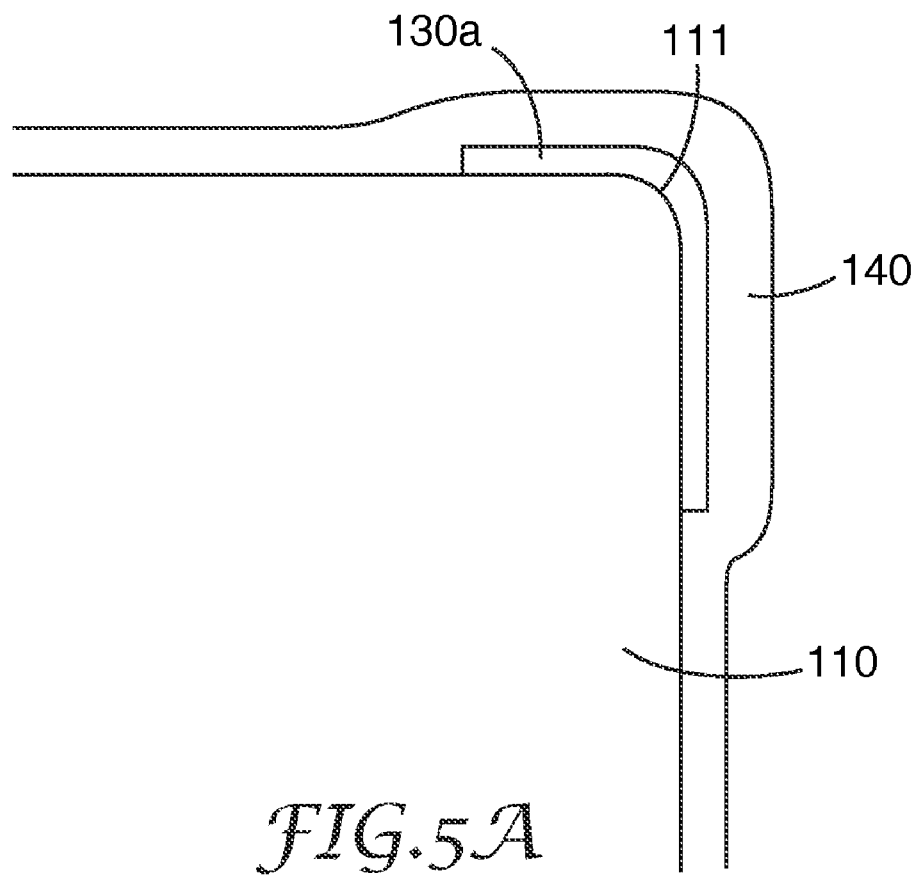
FIGS. 5A and 5B show alternative implementations of an exemplary sensor disposed on non-flat surfaces.
Figure 5B:
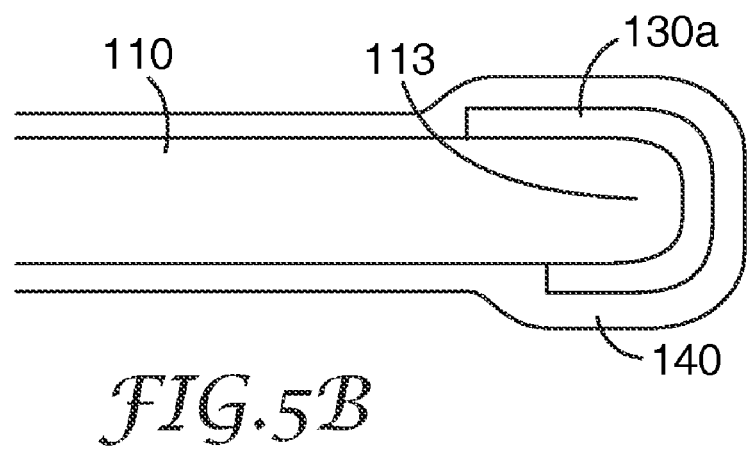

Using the above designs, exemplary embodiments of the detection system described herein can provide a non-disruptive, undercoating sensor. In addition, the sensors can be constructed on flexible, bendable substrates that allow a user to place sensors at critical areas of an engineered structure, such as non-flat surfaces (e.g., around bends and corners and other sharp-angled locations). These locations can be more susceptible to corrosion or other types of deteriorating events because protective coatings may not be evenly applied at corners and other sharp-angled locations. For example, as shown in FIGS. 5A and 5B, an exemplary sensor 130a can be disposed on a single corner surface 111 (FIG. 5A) or a multiple corner surface 113 (FIG. 5B) as might occur around the edge of an I-beam.

Thus, according to the above exemplary embodiments, embeddable corrosion sensors can be provided to detect moisture ingress, the ingress of species such as chlorides and other anionic species, coating curing, coating health, and structural health. As such sensors can be formed on flexible substrates, more location-specific real-time measurements can be provided to the user. Also, such thin circuits (e.g., ~0.001" thick) can be placed between a protective coating and the structure without adversely affecting the coating condition. Also, the data acquisition system can provide real time measurement of corrosion-related events. Such a corrosion sensor can help reduce the direct and indirect cost of corrosion related damage.

Various modifications, equivalent processes, as well as numerous structures to which the present invention may be applicable will be readily apparent to those of skill in the art to which the present invention is directed upon review of the present specification.

What is claimed is:

1. A detection system for monitoring a physical condition of an engineered structure, comprising:
    an array of sensors disposable in a predetermined pattern on the engineered structure and disposable between a surface of the engineered structure and a protective coating substantially covering the surface, wherein at least one sensor of the array comprises a sensing portion configured to detect at least one of an impedance, current, and voltage, the sensing portion disposed on a flexible substrate, and an optoelectronic interface to receive the optical signal generated by the controller
    a controller for retrieving data from the sensors, wherein the controller comprises a data acquisition system, a light source to generate the optical signal, an optical circulator, and an optical spectrum analyzer to receive returning optical signals from one or more of the sensors of the sensor array; and
    one or more optical fibers coupling an optical signal generated by the controller to the array of sensors, wherein the array of sensors provides data corresponding to at least one of a degree of cure of the protective coating, a health of the cured protective coating, and a corrosion rate of the engineered structure at each of the sensors.

2. The detection system of claim 1, wherein the light source comprises at least one of a continuous broadband source, a tunable laser source, and a series of narrowband light sources.

3. The detection system of claim 1, further comprising a tap-off device coupled to an optical fiber of the one or more optical fibers to distribute a portion of the optical signal to a sensor of the sensor array, wherein a remaining portion of the optical signal is distributed to other sensors of the sensor array.

4. The detection system of claim 3, wherein the optoelectronic interface of the sensor comprises an optical signal demultiplexer to select a predetermined optical channel and to send the selected optical signal along a first optical path and a remaining portion of the optical signal along a second path.

5. The detection system of claim 4, wherein the optoelectronic interface of the sensor further comprises an electrochromic switch disposed on the first optical path and a diode array disposed on the second optical path.

6. The detection system of claim 5, wherein the diode array comprises a PIN diode array that converts the remaining portion of the optical signal along the second path into an electrical signal that provides a power source for the electrochromic switch.

7. The detection system of claim 6, wherein the electrochromic switch includes at least first and second optically transmissive materials having a voltage-sensitive material disposed therebetween, wherein at least one of the optically transmissive materials further includes a high reflective coating disposed on a surface thereof.

8. The detection system of claim 7, wherein the electrochromic switch reflects a portion of the selected optical signal back along a first optical path and that is received by the controller, wherein the amount of the reflected optical signal corresponds to a condition of the protective coating.

9. The detection system of claim 6, wherein an amount of power available to power the electro-chromic switch corresponds to an impedance due to the sensing portion.

10. The detection system of claim 4, wherein the demultiplexer comprises a thin-film channel selector.

11. The detection system of claim 1, wherein the sensing portion is disposable on a non-flat surface of the engineered structure.

12. The detection system of claim 1, wherein the sensing portion comprises a conductive element patterned as at least two electrodes on the flexible substrate.

13. The detection system of claim 1, wherein the engineered structure comprises one of a metal, a composite material, a ceramic material, and fiberglass material.

14. The detection system of claim 1, wherein at least one sensor in the array comprises a sensing portion configured to corrode when exposed to a corrosive environment.

15. The detection system of claim 1, wherein at least one sensor in the array comprises a sensing portion having a thickness of from about 13 μm to about 75 μm.

16. The detection system of claim 1, wherein a first optical signal received by the optical spectrum analyzer has a first wavelength and corresponds to a first sensor of the array and wherein a second optical signal received by the optical spectrum analyzer has a second wavelength, different from the first wavelength, and corresponds to a second sensor of the array.

* * * * *

UNITED STATES PATENT AND TRADEMARK OFFICE
CERTIFICATE OF CORRECTION

PATENT NO. : 7,504,834 B2 Page 1 of 1
APPLICATION NO. : 11/613670
DATED : March 17, 2009
INVENTOR(S) : Ding Wang It is certified that error appears in the above-identified patent and that said Letters Patent is hereby corrected as shown below:

Column 4,
Line 18, after "1551 nm" insert -- ... --.

Signed and Sealed this

Fourteenth Day of July, 2009

JOHN DOLL
*Acting Director of the United States Patent and Trademark Office*